US006958348B2

(12) United States Patent  
Koya et al.

(10) Patent No.: US 6,958,348 B2
(45) Date of Patent: Oct. 25, 2005

(54) 3-GLYOXYLAMIDEINDOLES FOR TREATING CANCER

(75) Inventors: Keizo Koya, Brookline, MA (US); Lijun Sun, Harvard, MA (US); Mitsunori Ono, Lexington, MA (US); Guiqing Liang, Concord, MA (US); David James, Cambridge, MA (US); Hao Li, Brookline, MA (US); Zhi-Qiang Xia, Dedham, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 31 days.

(21) Appl. No.: 10/232,394

(22) Filed: Aug. 29, 2002

(65) Prior Publication Data

US 2003/0092751 A1 May 15, 2003

Related U.S. Application Data

(60) Provisional application No. 60/322,022, filed on Sep. 13, 2001.

(51) Int. Cl.$^7$ ............... A61K 31/435; C07D 453/02
(52) U.S. Cl. ............... 514/299; 514/439; 514/443; 514/380; 514/407; 514/411; 514/414; 546/135; 548/190; 548/206; 548/233; 548/245; 548/427
(58) Field of Search ............... 546/135; 549/457, 549/467; 514/299, 439, 443

(56) References Cited

U.S. PATENT DOCUMENTS

| | | | |
|---|---|---|---|
| 5,965,582 A | 10/1999 | Lebaut et al. | 514/338 |
| 6,008,231 A | 12/1999 | Lebaut et al. | 514/314 |
| 6,232,327 B1 | 5/2001 | Nickel et al. | 514/337 |
| 6,344,467 B1 | 2/2002 | Lebaut et al. | 514/339 |
| 6,500,853 B1 * | 12/2002 | Seehra et al. | 514/415 |
| 2003/0181482 A1 * | 9/2003 | Chen et al. | |
| 2004/0029858 A1 * | 2/2004 | Menta et al. | |

FOREIGN PATENT DOCUMENTS

| | | | |
|---|---|---|---|
| EP | 1157704 A1 | 11/2001 | |
| WO | 9943654 | * 2/1998 | |
| WO | WO 99/43654 | 9/1999 | |
| WO | WO 99/51224 | 10/1999 | |
| WO | WO 00/26202 | 5/2000 | |
| WO | WO 00/67802 | 11/2000 | |
| WO | WO 00/71535 A1 | 11/2000 | |
| WO | WO 02/08225 A1 | 1/2002 | |
| WO | WO 02/10152 A2 | 2/2002 | |

OTHER PUBLICATIONS

Patani et. al., "Bioisosterism: A Rational Approach in Drug Design", Chem. Rev. 1996, 96, pp. 3147–3176.*
See Ca 131:199619, "Preparation of indole derivatives as phospholipase enzyme inhibitors", Seehra. et al.*

* cited by examiner

Primary Examiner—Kamal A. Saeed
(74) Attorney, Agent, or Firm—Hamilton, Brook, Smith & Reynolds, PC

(57) ABSTRACT

Disclosed is an anti-cancer compound represented by Structural Formula (I):

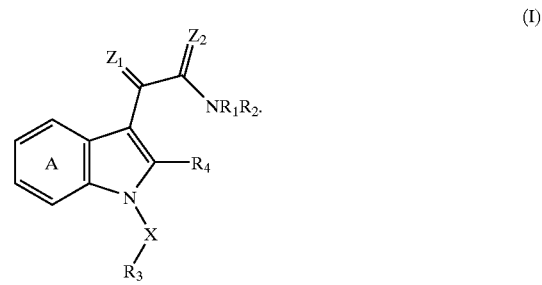

The variables in Structural Formula (I) are described hereinbelow. Also disclosed is a pharmaceutical composition comprising a pharmaceutically acceptable carrier or diluent and a compound represented by Structural Formula (I) (preferably an effective amount). Also disclosed is a method of treating a subject with cancer by administering to the subject an effective amount of a compound represented by Structural Formula (I).

16 Claims, 2 Drawing Sheets

3-GLYOXYLAMIDEINDOLES FOR TREATING CANCER

RELATED APPLICATIONS

The application claims the benefit of U.S. Provisional Application No. 60/322,022, filed Sep. 13, 2001, the entire teachings of which are incorporated herein by reference.

BACKGROUND OF THE INVENTION

Many methods are now available to be used in the treatment of cancer. Despite considerable advances, however, treatments for many cancers are inadequate for a number of reasons.

There are still cancers which simply do not respond or respond poorly to treatments are currently available. Patients with treatable cancers must often undergo chemotherapy with drugs that cause severe side effects. Few of these drugs can be used orally. Perhaps the most serious problem associated with cancer chemotherapy is the development of multi-drug resistance by many tumors. For example, many tumors which initially respond positively to an anti-cancer therapy by decreasing in size or even going into remission often develop resistance to the drug. Tumors that have developed resistance to more than one drug are said to be a "multi-drug resistant". There is little that can be done to halt or retard further progression of the disease, once a patient's cancer has become multi-drug resistant.

There is therefore still a need for new drugs which overcome one or more of the aforementioned shortcomings of drugs currently used in the treatment of cancer. Desirable properties of new anti-cancer drugs therefore include efficacy against tumors that are currently untreatable or poorly treatable, efficacy against multi-drug resistant tumors, oral bioavailability and/or reduced side effects.

SUMMARY OF THE INVENTION

It has now been found that 3-glyoxylamideindoles are cytotoxic against cancer cells, including multi-drug resistant cancer cells, from a number of different tissue types. For example, the $IC_{50}$ of Compounds (1)–(10) against the multi-drug resistant human uterine sarcoma cell line MES-SA/DX5 and the human myeloid leukemia cell line HL60/TX1000 was less than 0.1 $\mu$M (see Example 3–4 and 6). The structures of these compounds are shown in Example 2. In addition, the volume of tumors from the human breast cancer cell line MCF-5 in nude mice was reduced by greater than 50% when Compound (1) was administered intravenously every second day at doses of 10 mg/kg (Example 5); and the volume of tumors from the human breast cancer cell line MDA-435 in nude mice was reduced by greater than 50% when Compounds (3) and (5) were orally administered every second day at doses of 50 mg/kg and 25 mg/kg (Example 7). Little or no change in body weight was observed in mice treated with these compounds, indicating that they caused minimal side-effects. Based on these results, Compound (1) R=3-methyl-5-isothiazolyl
Compound (3) R=4-carboxamidephenyl
Compound (5) R=6-quinolinyl novel 3-glyoxylamideindoles, pharmaceutical compositions comprising these 3-glyoxylamideindoles and methods of treating subjects with cancer by administering 3-glyoxlylamideindoles are disclosed herein.

One embodiment of the present invention is a compound represented by Structural Formula (I):

(I)

Ring A is substituted or unsubstituted and is optionally fused to an aryl group.

$Z_1$ and $Z_2$ are independently =O, =S, =N—$OR_9$ or =$NR_9$.

$R_1$ is —H, an aliphatic group, a substituted aliphatic group, an unsubstituted aryl group or a substituted aryl group.

$R_2$ is an aryl group substituted with —C(O)—$NR_5R_6$, —S(O)$_2R_5R_6$ or —S(O)$R_5R_6$ or is an aryl group represented by a structural formula selected from (II)–(XI):

(II)

(III)

(IV)

-continued

Preferably, $R_2$ is an aryl group substituted with —C(O)—$NR_5R_6$, or is represented by Structural Formula (II), (V), (VII) or (XI).

$R_3$ is a substituted or unsubstituted aryl group or a substituted or unsubstituted aliphatic group.

$R_4$ is —H, a substituted alkyl group or an unsubstituted alkyl group.

$R_5$ and $R_6$ are independently —H, an aliphatic group, a substituted aliphatic group, an unsubstituted non-aromatic heterocylic group, a substituted non-aromatic heterocylic group, an unsubstituted aryl group or a substituted aryl group; or —$NR_5R_6$, taken together, is a substituted or unsubstituted non-aromatic nitrogen-containing heterocyclic group or a substituted or unsubstituted nitrogen-containing heteroaryl group.

X is a covalent bond, —C($R_7R_8$)—, —N($R_7$)—, —O—, —S—, —S(O)—, —S(O)$_2$—, —C(=O)—, —C(=O)—N($R_4$)—, or —N($R_7$)—C(=O)—.

$X_1$ is —O— or —S—.

$R_7$ and $R_8$ are independently —H or a substituted or unsubstituted aliphatic group;

$R_9$ is —H or a substituted or unsubstituted alkyl group.

Rings B–P are substituted or unsubstituted.

Another embodiment of the present invention is a compound represented by Structural Formula (XII):

(XII)

$Z_1$, $Z_2$ $R_4$ and Ring A are as described for Structural Formula (I).

Each $R_{15}$ is independently —Br, —Cl, —F, —$R_{18}$, —$OR_{18}$, —CN, —$COOR_{18}$, —$N(R_{18})_2$, —$CON(R_{18})_2$, —$NR_{18}COR_{19}$, —$NHCONH_2$ and —$SO_2$ $N(R_{18})_2$.

n is an integer from 0–4.

$R_{16}$ and $R_{17}$ are independently —H, an aliphatic group, a substituted aliphatic group, an unsubstituted non-aromatic heterocylic group, a substituted non-aromatic heterocylic group, an unsubstituted aryl group or a substituted aryl group; or —$NR_{16}R_{17}$, taken together, is a substituted or unsubstituted non-aromatic nitrogen-containing heterocyclic group or a substituted or unsubstituted nitrogen-containing heteroaryl group.

Each $R_{18}$ and $R_{19}$ are independently selected from —H, alkyl or substituted alkyl.

Another embodiment of the present invention is a pharmaceutical composition comprising a pharmaceutically acceptable carrier or diluent and a compound represented by Structural Formula (I) or (XII). Preferably, the pharmaceutical composition comprises an effective amount of the compound. The pharmaceutical compositions can be used in therapy, e.g., in the treatment of cancer.

Another embodiment is a method of treating a subject with cancer. The method comprises administering to the subject an effective amount of a compound represented by Structural Formula (I) or (XII).

Another embodiment of the present invention is the use of a compound represented by Structural Formula (I) or (XII) for the manufacture of a medicament for the treatment of cancer. The medicament comprises an effective amount of the compound represented by Structural Formula (I) or (XII).

The disclosed 3-glyoxylamideindoles have many advantages when used to treat cancers. Most significantly, they are cytotoxic to many multi-drug resistant cell lines and therefore can be used when other traditional cancer chemotherapies have failed. In addition, they exhibit minimal side effects and are active when administered orally.

DETAILED DESCRIPTION OF THE INVENTION

In Structural Formula (I), preferably Ring A is substituted or unsubstituted; $Z_1$ and $Z_2$ are both =O; $R_1$ and $R_4$ are both —H; $R_3$ is a substituted or unsubstituted aryl group; X is a —C($R_7R_8$)—, —N($R_7$)— and —O— (preferably —C($R_7R_8$)—); and the remainder of the variables are as described above.

More preferably in Structural Formula (I), Ring A is substituted or unsubstituted; $Z_1$ and $Z_2$ are both =O; $R_1$ and $R_4$ are both —H; $R_3$ is a substituted or unsubstituted phenyl or pyridyl group; X is a —C($R_7R_8$)—, —N($R_7$)— and —O— (preferably —C($R_7R_8$)—); $R_7$ and $R_8$ are both H; and the remainder of the variables are as described above.

As noted above, $R_2$ is preferably is an aryl group substituted with —C(O)—$NR_5R_6$ or is represented by Structural Formula (II), (V), (VII) or (XII). More preferably, $R_2$ is represented by a Structural Formula selected from (XIII)–(XVII);

(XIII)

(XIV)

(XV)

(XVI)

(XVII)

In Structural Formulas (XIII)–(XVII), $X_2$ is —N— or —CH— and $R_{12}$ and $R_{13}$ are independently a C1–C4 alkyl group. Preferably in Structural Formulas (XIII)–(XVII), $X_2$ is —N— or —CH—; $R_{12}$ and $R_{13}$ are independently a C1–C4 alkyl group; and $R_5$ and $R_6$ are independently —H or a C1–C4 alkyl group.

In Structural Formula (XII), preferably Ring A is substituted or unsubstituted, $Z_1$ and $Z_2$ are =O; $R_4$ is —H; each $R_{15}$ is independently —Cl, —F, —$R_{18}$, —$OR_{18}$, —CN, —$NH_2$, —$CONH_2$ or —$NHCOR_{18}$; n is 0 or 1 (more preferably 0); $R_{16}$ is —H; $R_{17}$ is a substituted or unsubstituted aryl group; $R_{18}$ is a C1–C4 alkyl group; and the remainder of the variables are as described above. Preferred aryl groups for $R_{17}$ include substituted or unsubstituted phenyl, pyridyl (e.g., 4-pyridyl), pyrimidyl and quinolinyl. Examples of preferred substituents for these aryl group include —Cl, —Br, —F, C1–C6 alkyl, C1–C6 alkoxy, C1–C6 haloalkyl, C1–C6 haloalkoxy, —CN, —OH, -Obenzyl, —$NO_2$, —$NH_2$, C1–C6 alkylamine, C1–C6alkoxycarbonylamino, COOH, COO(C1–C6 alkyl) and C3-C cycloalkyl.

The term "aryl group" refers to carbocyclic aromatic groups such as phenyl, naphthyl, and anthracyl, and heteroaryl groups such as imidazolyl, isoimidazolyl, thienyl, furanyl, pyridyl, pyrimidyl, pyranyl, pyrazolyl, pyrrolyl, pyrazinyl, thiazoyl, isothiazolyl, oxazolyl, isooxazolyl, 1,2, 3-trizaolyl, 1,2,4-triazolyl, and tetrazolyl.

Aryl groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazolyl, benzoisothiazolyl, benzooxazolyl, benzoisooxazolyl, benzimidazolyl, quinolinyl, isoquinolinyl and isoindolyl.

An aliphatic group is a straight chained, branched or cyclic non-aromatic hydrocarbon which is completely saturated or which contains one or more units of unsaturation. Typically, a straight chained or branched aliphatic group has from 1 to about 10 carbon atoms, preferably from 1 to about 4, and a cyclic aliphatic group has from 3 to about 10 carbon atoms, preferably from 3 to about 8. An aliphatic group is preferably a straight chained or branched alkyl group, e.g, methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1–C4 straight chained or branched alkyl group or a C3–C8 cyclic alkyl group is also referred to as a "lower alkyl" group.

An "alkylene group" is represented by —$(CH_2)_n$—. n is an integer from 1–10, preferably 1–4.

Non-aromatic heterocyclic rings are non-aromatic carbocyclic rings which include one or more heteroatoms such as nitrogen, oxygen or sulfur in the ring. The ring can be five, six, seven or eight-membered. Examples include oxazolinyl, thiazolinyl, oxazolidinyl, thiazolidinyl, tetrahydrofuranyl, tetrahyrothiophenyl, morpholino, thiomorpholino, pyrrolidinyl, piperazinyl, piperidinyl, and thiazolidinyl.

Suitable substituents for an aliphatic group, non-aromatic heterocyclic group, benzylic or an aryl group ring carbon (carbocyclic and heteroaryl) are those which do not substantially interfere with the anti-cancer activity of the disclosed compounds. Examples of suitable substituents include —OH, halogen (—Br, —Cl, —I and —F), —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—N($R^aR^b$), —C(=$NR^c$)—$NH_2$, —C(=$NR^c$)—$NHR^a$, —C(=$NR^c$)—N($R^aR^b$), —NH—C(=NH)—$NH_2$, —NH—C(=NH)—$NHR^a$, —NH—C(=NH)—N($R^aR^b$), —NH—C(=$NR^c$)—$NH_2$, —NH—C(=$NR^c$)—$NHR^a$, —NH—C(=$NR^c$)—N($R^aR^b$),

—NR$^d$H—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SO$_k$R$^a$ (k is 0, 1 or 2) and —NH—C(=NH)—NH$_2$. R$^a$–R$^d$ are each independently an aliphatic, substituted aliphatic, benzyl, substituted benzyl, aryl or substituted aryl group, preferably an alkyl, benzylic or aryl group. In addition, —NR$^a$R$^d$, taken together, can also form a substituted or unsubstituted non-aromatic heterocyclic group. A non-aromatic heterocyclic group, benzylic group or aryl group can also have an aliphatic or substituted aliphatic group as a substituent. A substituted aliphatic group can also have a non-aromatic heterocyclic ring, a substituted a non-aromatic heterocyclic ring, benzyl, substituted benzyl, aryl or substituted aryl group as a substituent. A substituted aliphatic, non-aromatic heterocyclic group, substituted aryl, or substituted benzyl group can have more than one substituent.

Suitable substituents for heteroaryl ring nitrogen atoms having three covalent bonds to other heteroaryl ring atoms include —OH and -alkoxy (preferably C1–C4). Substituted heteroaryl ring nitrogen atoms that have three covalent bonds to other heteroaryl ring atoms are positively charged, which is balanced by counteranions such as chloride, bromide, formate, acetate and the like. Examples of other suitable counteranions are provided in the section below directed to suitable pharmacologically acceptable salts.

Suitable substituents for heteroaryl ring nitrogen atoms having two covalent bonds to other heteroaryl ring atoms include alkyl, substituted alkyl (including haloalkyl), phenyl, substituted phenyl, —C(O)(alkyl), —S(O)$_2$-(alkyl), —S(O)$_2$—NH(alkyl) and —S(O)$_2$—NH(alkyl)$_2$.

Preferred substituents for Ring A include —F, —Cl, —Br, —C1–C4 alkyl, C1–C4 alkoxy, —C1–C4 haloalkyl, C1–C4 haloalkoxy, —CN or —NH$_2$. Ring A can have zero, one or more substituents.

Aryl Rings B–P can be substituted with zero, one or more independently selected substituents, suitable examples for which are described above. Preferred substituents for ring carbon atoms of Aryl Rings B–P include C1–C4 alkyl, C1–C4 hydroxyalkyl, N-morpholino, pyrimidyl, C1–C4 alkyl substituted with pyrimidyl, —NH(C1–C4 alkyl), —N(C1–C4 alkyl)$_2$, —C(O)NH$_2$, —C(O)NH(C1–C4 alkyl), C(O)N(C1–C4 alkyl)$_2$, —NHC(O)(C1–C4 alkyl), —NO$_2$, C1–C4 alkoxy, —C(O)O—CH$_2$CH$_2$—N(C1–C4 alkyl)$_2$, —C(O)O—CH$_2$CH$_2$—NH(C1–C4 alkyl), —NH—(phenyl), —NH$_2$, —CH$_2$NH—C(O)—O—(C1–C4 alkyl), —CH$_2$NH$_2$, —Cl, —F, —C(O)—O—(C1–C4 alkyl), —C(O)—NH—(C1–C4 alkyl), C3–C7 cycloalkyl, phenyl, —C(O)—N-morpholino, —S—(C1–C4 alkyl), —CN, furyl, —S(O)$_2$—(C1–C4 alkyl), —S(O)$_2$—NH$_2$, —S(O)$_2$—NH (C1–C4 alkyl), —S(O)$_2$—N(C1–C4 alkyl)$_2$.

Preferred substituents for the phenyl and pyridyl ring represented by R$_3$ and suitable values for R$_{15}$ include —Br, —Cl, —F, —R$^e$, —OR$^e$, —CH$_3$, —CF$_3$, —CN, —COOR$^e$, —N(R$^e$)$_2$, —CON(R$^e$)$_2$, —NR$^e$COR$^f$, —NHCONH$_2$, —SO$_2$R$^e$ and —SO$_2$N(R$^e$)$_2$. Each R$^e$ and R$^f$ are independently selected from —H, alkyl or substituted alkyl. More preferred substituents for the phenyl group represented by R$_3$ and more preferred values for R$_{15}$ include —Cl, —F, —R$^e$, —OR$^e$, —CN, —NH$_2$, —CONH$_2$ or —NHCOR$^f$. Even more preferred substituents for the phenyl group represented by R$_3$ and even more preferred values for R$_{15}$ include —CH$_3$, —CH$_2$CH$_3$, —F, —Cl, —CN or —OCH$_3$. The phenyl ring represented by R$_3$ can have zero, one or more substituents but is preferably unsubstituted or monosubstituted substituted. When monosubstituted, the substituent is preferably at the position para to the carbon atom bonded to the methylene group.

Also included in the present invention are pharmaceutically acceptable salts of the compounds described herein. Compounds disclosed herein which possess a sufficiently acidic, a sufficiently basic, or both functional groups, and accordingly can react with any of a number of organic or inorganic bases, and inorganic and organic acids, to form a salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

The disclosed compounds can be used to treat subjects with cancer, including multi-drug resistant cancers. A cancer is resistant to a drug when it resumes a normal rate of tumor growth while undergoing treatment with the drug after the tumor had initially responded to the drug. A tumor "responds to a drug" when it exhibits a decrease in tumor mass or a decrease in the rate of tumor growth. The term "multi-drug resistant cancer" refers to cancer that is resistant to two or more drugs, typically five or more.

An "effective amount" is the quantity of compound in which a beneficial clinical outcome is achieved when the compound is administered to a subject with a multi-drug resistant cancer. A "beneficial clinical outcome" includes a reduction in tumor mass, a reduction in the rate of tumor mass increase, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of cancer. The skilled artisan will be able to determine appropriate dosages depending on these and other factors. Effective amounts of the disclosed compounds typically range between about 1 mg/mm$^2$ per day and about 10 grams/mm$^2$ per day, and preferably between 10 mg/mm2 per day and about 5 grams/mm$^2$.

The disclosed compounds are administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compounds can also be administered orally (e.g., dietary), topically, by inhalation (e.g., intrabronchial, intranasal, oral inhalation or intranasal drops), or rectally, depending on the type of cancer to be treated. Oral or parenteral administration are preferred modes of administration.

The disclosed compounds can be administered to the subject in conjunction with an acceptable pharmaceutical carrier as part of a pharmaceutical composition for treatment of cancer. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrasn) are known in the art (Baker, et al., "Controlled Release of Biological Active Agents", John Wiley and Sons, 1986).

Optionally, the disclosed compounds can be co-administered with other anti-cancer agents such as Taxol, Vincristine, Adriamycin, Etoposide, Doxorubicin. Dactinomycin, Mitomycin C, Bleomycin, Vinblastine, Cisplatin and the like. Preferably, the disclosed compounds are co-administered before the cancer develops multi-drug resistance or as the cancer is developing multi-drug resistance but before the cancer becomes completely resistant to the anticancer drugs being used. The method can also be carried in combination with other cancer treatments such as surgery, radiation, and the like.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

Procedures for preparing the compounds of the present invention are provided in Example 1, below.

The present invention is illustrated by the following examples, which are not intended to be limiting in any way.

EXEMPLIFICATION

Example 1

Preparation of 2-(1-(4-Chloro-benzyl)-1-indol-3-yl)-N-(3-methyl-isothiazol-5-yl)-2-oxo-acetamide (Compound (1))

The solution of oxalyl chloride (0.44 ml, 5.1 mmol) in ethyl ether (25 mL) was cooled in an ice-bath. To it was added 1-(4'-chlorobenzyl)-indole (1.01 g, 4.14 mmol) in ethyl ether (25 mL). The resulting yellow slurry was refluxed for 2 hours. After removal of solvent in vacuo, the residue was dissolved in THF (20 mL) and cooled to 0° C. 5-Amino-3-methylisothiazole (1.32 g, 9.73 mmol) in THF (20 mL) was added dropwise. The mixture was then warmed to room temperature, and stirred overnight. Solvent was removed in vacuo. Silica gel chromatographic purification gave the product (1.49 g) in 88% yield (R$_f$ 0.3, 1:1 ethyl acetate/hexane).$^1$H NMR (DMSO-d$_6$) δ 2.37 (s, 3H), 5.67 (s, 2H), 7.07 (s, 1H), 7.36 (m, 6H), 7.61 (d, J=9.0 Hz, 1H), 8.32 (d, J=8.1 Hz, 1H), 9.18 (s, 1H). ESMS calcd (C$_{21}$H$_{16}$ClN$_3$O$_2$S): 409.1; found: 408.1 (M−H)$^+$.

Example 2

Synthesis of 2-[1-(4-Chloro-benzyl)-1H-indol-3-yl]-2-hydroxyimino-N-(3-methyl-isothiazol-5-yl)-acetamide A stirred mixture of 2-[1-(4-chlorobenzyl)-1H-indol-3-yl]-N-(3-methyl-isothiazol-5-yl)-2-oxo-acetamide (0.102 g, 0.25 mmol), hydroxylamine hydrochloride (17 mg, 0.25 mmol), and sodium acetate (0.1 g, 1.2 mmol) in EtOH (3 mL) and THF (3 mL) was heated to reflux for 3 days. After being cooled to rt, the reaction mixture was poured into ice-H$_2$O (20 mL). The precipitated product 2-[1-(4-Chlorobenzyl)-1H-indol-3-yl]-2-hydroxyimino-N-(3-methylisothiazol-5-yl)-acetamide was collected by filtration, washed with H$_2$O, and dried in vacuo (95 mg, 90%). $^1$H NMR (DMSO-d$_6$) δ 2.3 (s, 3H), 5.6 (s, 2H), 6.9 (s, 1H), 7.0–7.5 (m, 7H), 8.1 (d, 1H, J=7), 8.65 (s, 1H). ESMS calcd for (C$_{21}$H$_{17}$ClN$_4$O$_2$S): 424.1; found 425.1 (M+H)$^+$.

The following compounds were synthesized according to similar procedures described above.

Compound (1)

$^1$H NMR (DMSO-d$_6$): δ 2.37 (s, 3H), 5.67 (s, 2H), 7.07 (s, 1H), 7.36 (m, 6H), 7.61 (d, J=9.0 Hz, 1H), 8.32 (d, J=8.1 Hz, 1H), 9.18 (s, 1H). ESMS calcd C$_{21}$H$_{16}$ClN$_3$O$_2$S): 409.1; found: 408.1 (M−H)$^+$.

Compound (2)

$^1$H NMR (DMSO-d$_6$): δ 3.46 (s, 3H), 5.90 (s, 2H), 7.18 (s, 1H), 7.60 (m, 5H), 7.93 (d, J=7.8 Hz, 2H), 8.44 (m, 1H), 9.32 (s, 1H), 10.38 (s, 1H). ESMS calcd (C$_{22}$H$_{16}$N$_4$O$_2$S): 400.1; found: 401.1 (M+H)$^+$.

Compound 3

$^1$H NMR (DMSO-d$_6$): δ 10.93(s, 1H), 9.04(s, 1H), 8.32(d, 1H), 7.89(m, 5H), 7.61(d, 1H), 7.43(d, 2H), 7.32(m, 5H), 5.63(s, 2H); ESMS Calcd (C$_{24}$H$_{18}$ClN$_3$O$_3$): 431.10, found: 432.1 (M+H)$^+$.

Compound (4)

$^1$H NMR (DMSO-d$_6$): δ 5.63 (s, 2H), 7.33 (m, 4H), 7.42 (d, 2H), 7.54 (s, 1H), 7.61 (m, 1H), 8.11 (s, 1H), 8.28 (m, 3H), 8.87 (s, 1H), 8.98 (s, 1H), 10.79 (s, 1H); ESMS Calcd (C$_{23}$H$_{17}$ClN$_4$O$_3$): 432.10; found: 433.2 (M+H)$^+$.

Compound (5)

$^1$H NMR (DMSO-d$_6$): δ 11.09(s, 1H), 9.08(d, 1H), 8.85(d, 1H), 8.67(s, 1H), 8.34(m, 2H), 8.09(d, 1H), 8.02(d, 1H), 7.62(d, 1H), 7.53(m, 1H), 7.3–7.3(m, 6H), 5.64(s, 2H); ESMS Calcd (C$_{26}$H$_{18}$ClN$_3$O$_2$): 439.11, found: 440.1 (M+H)$^+$.

Compound (6)

¹H NMR (DMSO-d₆) δ 2.65 (s, 3H), 4.73 (s, 2H), 7.48 (m, 7H), 7.73 (d, J=9.0 Hz, 1H), 8.37 (d, J=9.0 Hz, 1H), 8.96 (s, 1H). ESMS calcd (C$_{20}$H$_{16}$ClN$_5$O$_2$S): 425.1; found: 426.1 (M+H)$^+$.

Compound (9)

¹H NMR (DMSO-d₆): δ 11.12(s, 1H), 9.06(s, 1H), 8.53(d, 2H), 8.32(d, 1H), 7.85(m, 4H), 7.57(d, 1H), 7.46(d, 2H), 7.31(m, 2H), 5.76(s, 2H); ESMS Calcd (C$_{23}$H$_{16}$N$_4$O$_2$): 380.13, found: 381.1 (M+H)$^+$.

Compound (7)

¹H NMR (DMSO-d₆) δ 5.41 (s, 2H), 7.15 (d, J=8.1 Hz, 2H), 7.32 (m, 6H), 8.40 (s, 1H), 8.50 (d, J=7.8 Hz, 1H), 9.04 (s, 1H), 10.04 (s, 1H). ESMS calcd (C$_{20}$H$_{14}$ClN$_3$O$_3$): 379.1; found: 378.1 (M−H)$^+$.

Compound (10)

¹H NMR (DMSO-d₆): δ 2.34 (s, 3H), 5.42 (s, 2H), 6.38 (s, 1H), 7.15 (d, J=8.1 Hz, 2H), 7.30 (m, 5H), 8.48 (d, J=8.1 Hz, 1H), 9.04 (s, 1H), 10.09 (s, 1H). ESMS calcd (C$_{21}$H$_{16}$ClN$_3$O$_3$): 393.1; found: 394.1 (M+H)$^+$.

Compound (8)

¹H NMR (DMSO-d₆): δ 4.24 (s, 3H), 7.42 (m, 8H), 7.83 (m, 2H), 8.35 (m, 2H), 8.66 (m, 2H), 8.95 (m, 1H), 9.33 (s, 1H), 9.78 (s, 1H). ESMS calcd (C$_{26}$H$_{20}$N$_4$O$_2$): 420.2; found: 421.2 (M+H)$^+$.

Compound (11)

¹H NMR (DMSO-d₆) δ 0.94 (m, 4H), 1.92 (m, 1H), 3.46 (s, 3H), 5.73 (s, 2H), 6.14 (s, 1H), 7.48 (m, 5H), 7.72 (d, J=9.3 Hz, 1H), 8.41 (d, J=9.3 Hz, 1H), 9.08 (s, 1H), 9.27 (s, 1H). ESMS calcd (C$_{24}$H$_{21}$ClN$_4$O$_2$): 432.1; found: 433.1.1 (M+H)$^+$.

Compound (12)

¹H NMR (DMSO-d₆) δ 1.31 (s, 9H), 5.64 (s, 2H), 6.95 (s, 1H), 7.46 (m, 7H), 7.70 (m, 1H), 8.26 (d, J=5.1 Hz, 1H), 8.98 (s, 1H). ESMS calcd ($C_{24}H_{22}ClN_3O_2S$): 451.1; found: 450.1 (M−H)⁺.

Compound (13)

¹H NMR (DMSO-d₆) δ 5.67 (s, 1H), 7.60 (m, 14H), 8.31 (m, 2H), 8.90 (s, 1H). ESMS calcd ($C_{27}H_{20}ClN_5O_3$): 497.1; found: 498.1 (M+H)⁺.

Compound (14)

¹H NMR (DMSO-d₆): δ 5.74 (s, 2H), 6.74 (s, 1H), 6.99 (m, 2H), 7.47 (m, 6H), 7.72 (m, 1H), 7.91 (s, 1H), 8.40 (m, 1H), 9.08 (s, 1H). ESMS calcd ($C_{24}H_{17}ClN_4O_3$): 444.1; found: 443.1 (M−H)⁺.

Compound (15)

¹H NMR (DMSO-d₆): δ 2.61 (s, 3H), 5.24 (s, 2H), 7.26 (d, J=8.1 Hz, 2H), 7.39 (m, 8H), 8.63 (d, J=6.6 Hz, 1H), 9.15 (s, 1H). ESMS calcd ($C_{21}H_{16}ClN_3O_2S$): 409.1; found: 408.1 (M−H)⁺.

Compound (16)

¹H NMR (DMSO-d₆): δ 5.38 (s, 2H), 7.30 (m, 7H), 7.88 (m, 1H), 8.57 (m, 2H), 8.89 (s, 1H). ESMS calcd ($C_{19}H_{14}ClN_5O_2$): 379.1; found: 378.1 (M−H)⁺.

Compound (17)

¹H NMR (DMSO-d6): δ 5.76 (s, 2H), 7.44 (m, 6H), 7.73 (d, J=7.5 Hz, 2H), 7.95 (s, 1H), 8.29 (s, 1H), 8.42 (d, J=7.5 Hz, 1H), 9.27 (s, 1H). ESMS calcd ($C_{21}H_{16}ClN_5O_3$): 421.1; found: 420.1 (M−H)⁺.

Compound (18)

Compound (21)

¹H NMR (DMSO-d₆): δ 2.48 (s, 3H), 5.41 (s, 2H), 6.79 (s, 1H), 7.15 (d, J=8.1 Hz, 2H), 7.33 (m, 5H), 6.50 (d, J=7.8 Hz, 1H), 9.04 (s, 1H), 9.88 (s, 1H). ESMS calcd (C$_{21}$H$_{16}$ClN$_3$O$_3$): 393.1; found: 394.1 (M+H)⁺.

¹H NMR (DMSO-d₆): δ 5.78 (s, 2H), 7.48 (m, 6H), 7.75 (m, 1H), 7.91(d J=9.6 Hz, 1H), 8.28 (d, J=9.9 Hz, 1H), 8.46 (m, 1H), 9.20 (s, 1H). ESMS calcd C$_{24}$H$_{15}$ClN$_4$O$_4$S): 490.1; found: 489.1 (M−H)⁺.

Compound (19)

Compound (22)

¹H NMR (DMSO-d₆): δ 1.51 (t, J=7.5, 3H), 3.35 (q, J=7.2 Hz, 2H), 5.43 (s, 2H), 7.26 (d, J=8.1 Hz, 2H), 7.35 (m, 5H), 8.50 (d, J=7.2 Hz, 1H), 9.04 (s, 1H), 10.91 (s, 1H). ESMS calcd (C$_{20}$H$_{15}$ClN$_4$O$_2$S$_2$): 442.0; found: 443.1 (M−H)⁺.

¹H NMR (DMSO-d₆): δ 4.12 (s, 3H), 5.36 (s, 2H), 6.68(d, J=7.8 Hz, 1H), 7.37 (m, 9H), 8.50 (d, J=9.9 Hz, 1H), 9.15 (s, 1H), 10.51 (s, 1H). ESMS calcd C$_{25}$H$_{18}$ClN$_3$O$_4$): 459.1; found: 460.1 (M+H)⁺.

Compound (20)

Compound (23)

¹H NMR (DMSO-d6): δ 5.41 (s, 2H), 7.14 (d, J=8.4 Hz, 2H, 7.34 (m, 5H), 8.48 (d, J=9.5 Hz, 1H), 8.95 (s, 1H), 9.04 (s, 1H), 10.91 (s, 1H). ESMS calcd C$_{19}$H$_{13}$ClN$_4$O$_2$S): 396.0; found: 397.0 (M+H)⁺.

¹H NMR (DMSO-d₆): δ 5.39 (s, 2H), 7.14 (d, J=8.4 Hz, 2H), 7.56 (m, 6H), 7.71 (m, 2H), 8.24 (d, J=9.0 Hz, 1H), 8.49 (d, J=7.8 Hz, 1H), 10.07 (s, 1H). ESMS calcd C$_{24}$H$_{16}$ClN$_3$O$_3$): 429.1; found: 430.1 (M+H)⁺.

Compound (24)

¹H NMR (DMSO-d₆): δ 2.67 (s, 3H), 5.40 (s, 2H), 7.15 (d, J=8.4 Hz, 1H), 7.36 (m, 5H), 8.57 (d, J=7.2 Hz, 1H), 9.03 (s, 1H), 10.19 (s, 1H). ESMS calcd $C_{21}H_{15}Cl_2N_3O_2S$: 443.0; found: 444.1 (M+H)⁺.

Compound (25)

¹H NMR (DMSO-d₆): δ 5.51 (s, 2H), 6.64 (m, 1H), 7.26 (d, J=8.4 Hz, 2H), 7.44 (m, 5H), 8.38 (m, 1H), 8.56 (d, J=8.1 Hz, 1H), 9.15 (s, 1H), 10.33 (s, 1H). ESMS calcd $C_{20}H_{14}ClN_3O_3$: 379.1; found: 380.1 (M+H)⁺.

Compound (26)

¹H NMR (DMSO-d₆): δ 5.87 (s, 2H), 7.66 (m, 6H), 7.94 (d, J=7.8 Hz, 2H), 8.23 (m, 2H), 8.44 (d, J=7.5 Hz, 2H), 8.78 (s, 1H), 8.95 (m, 1H), 9.23 (s, 1H), 11.21 (s, 1H). ESMS calcd ($C_{27}H_{18}N_4O_2$): 430.1; found: 431.1 (M+H)⁺.

Compound (27)

¹H NMR (DMSO-d₆): δ 0.89 (t, 3H), 1.49(q, 2H), 3.21 (m, 2H), 5.61 (s, 2H), 7.25(m, 5H), 7.60 (m, 1H), 7.86 (d, 2H), 7.94 (d, 2H), 8.29 (d, 1H), 8.40 (t, 1H), 10.91 (s, 1H); ESMS Calcd ($C_{27}H_{24}ClN_3O_3$): 473.15; found: 472.0 (M−H)⁺.

Compound (28)

¹H NMR (DMSO-d₆): δ 2.94 (s, 6H), 5.63 (s, 2H), 7.38 (m, 9H), 7.62 (dd, 1H), 7.86 (d, 2H), 8.30 (dd, 1H), 9.01 (s, 1H); ESMS Calcd ($C_{26}H_{22}ClN_3O_3$): 459.13; found: 460.3 (M+H)⁺.

Compound (29)

¹H NMR (DMSO-d₆): δ 2.77 (s, 3H), 5.62 (s, 2H), 7.34 (m, 3H), 7.42 (d, 2H), 7.62 (m, 1H), 7.85 (d, 2H), 7.95 (d, 2H), 8.30 (m, 1H), 8.39 (m, 1H), 9.03 (s, 1H); ESMS Calcd ($C_{25}H_{20}ClN_3O_3$): 445.12; found: 446.1 (M+H)⁺.

Compound (30)

¹H NMR (DMSO-d₆): δ 3.53 (m, 8H), 5.63 (s, 2H), 7.37 (m, 8H), 7.60 (d, 1H), 7.93 (d, 2H), 8.29 (d, 1H), 9.00 (s, 1H), 10.92 (s, 1H); ESMS Calcd ($C_{28}H_{24}ClN_3O_4$): 501.15; found: 502.1 (M+H)⁺.

Compound (31)

¹H NMR (DMSO-d₆): δ 10.94(s, 1H), 9.07(s, 1H), 8.31(d, 1H), 7.93(m, 5H), 7.82(d, 2H), 7.58(d, 1H), 7.46(d, 2H), 7.33(m, 3H), 5.76(s, 2H); ESMS Calcd ($C_{25}H_{18}N_4O_3$); 422.14, found: 423.1 (M+H)⁺.

Compound (32)

¹H NMR (DMSO-d₆): δ 11.12(s, 1H), 7.94(s, 1H), 7.93(d, 2H), 7.80(d, 2H), 7.52(m, 2H), 7.41(d, 2H), 7.34(s, 1H), 7.07(d, 2H), 6.89(d, 1H), 5.57(s, 2H), 3.68(s, 3H), 2.61(s, 3H); ESMS Calcd ($C_{26}H_{22}ClN_3O_4$): 475.13, found: 476.1 (M+H)⁺.

Compound (33)

¹H NMR (DMSO-d₆); δ 10.84(s, 1H), 9.06(s, 1H), 8.43(s, 1H), 8.31(m, 1H), 7.97(s, 1H), 7.90(d, 1H), 7.63(m, 2H), 7.3–7.48(m, 8H), 5.63(s, 2H); ESMS Calcd ($C_{24}H_{18}ClN_3O_3$): 431.10, found: 432.1 (M+H)⁺.

Compound (34)

¹H NMR (DMSO-d₆): δ 12.88(s, 1H), 9.21(s, 1H), 8.69(d, 1H), 8.31(m, 2H), 7.87(d, 1H), 7.84(s, 1H), 7.59(m, 2H), 7.2–7.4(m, 6H), 5.65(s, 2H); ESMS Calcd ($C_{24}H_{18}ClN_3O_3$): 431.10, found: 432.1 (M+H)⁺.

Compound (35)

¹H NMR (DMSO-d₆): δ 11.12(s, 1H), 8.97(s, 1H), 8.42(s, 1H), 8.30(m, 1H), 8.22(s, 1H), 7.60(m, 1H), 7.3–7.4(m, 7H), 5.64(s, 2H); ESMS Calcd ($C_{24}H_{14}ClF_4N_3O_3$): 503.07 found: 503.7 (M+H)⁺.

Compound (36)

¹H NMR (DMSO-d₆): δ 12.89(s, 1H), 9.25(s, 1H), 8.68(d, 1H), 8.32(m, 2H), 7.82(m, 4H), 7.56(m, 2H), 7.45(d, 2H), 7.32(m, 2H), 7.24(m, 1H), 5.77(s, 2H); ESMS Calcd ($C_{25}H_{18}N_4O_3$): 422.14, found: 423.1 (M+H)⁺.

Compound (37)

¹H NMR (DMSO-d₆): δ 11.13(s, 1H), 9.01(s, 1H), 8.42(s, 1H), 8.30(d, 1H), 8.22(s, 1H), 7.82(d, 2H), 7.57(d, 1H), 7.43(d, 2H), 7.32(m, 2H), 5.76(s, 2H); ESMS Calcd ($C_{25}H_{14}F_4N_4O_3$): 494.10, found: 495.1 (M+H)⁺.

Compound (38)

¹H NMR (DMSO-d₆): δ 11.08(s, 1H), 9.06(s, 1H), 8.31(d, 1H), 8.01(m, 4H), 7.81(d, 2H), 7.58(d, 1H), 7.46(d, 2H), 7.32(m, 2H), 5.74(s, 2H), 3.84(s, 3H); ESMS Calcd ($C_{26}H_{19}N_3O_4$): 437.14, found: 438.1 (M+H)⁺.

Compound (39)

¹H NMR (DMSO-d₆): δ 11.06(s, 1H), 9.03(s, 1H), 8.29(d, 1H), 8.03(d, 2H), 7.82(d, 2H), 7.61(d, 1H), 7.3–7.4(m, 8H), 5.63(s, 2H); ESMS Calcd ($C_{23}H_{18}ClN_3O_4S$): 467.07, found: 468.1 (M+H)⁺.

Compound (40)

¹H NMR (DMSO-d₆): δ 11.03(s, 1H), 9.07(s, 1H), 8.61(s, 1H), 8.34(d, 1H), 8.22(d, 1H), 8.04(d, 1H), 7.92(d, 1H), 7.62(d, 1H), 7.3–7.4(m, 7H), 5.64(s, 2H), 2.65(s, 3H); ESMS Calcd ($C_{27}H_{20}ClN_3O_2$): 453.12, found: 454.1 (M+H)⁺.

Compound (41)

¹H NMR (DMSO-d₆,): δ 10.93(s, 1H), 9.08(s, 1H), 8.41(t, 1H), 8.31(d, 1H), 7.96(d, 2H), 7.88(d, 2H), 7.82(d, 2H), 7.57(d, 1H), 7.46(d, 2H), 7.31(m, 2H), 5.75(s, 2H), 3.21(q,

2H), 1.52(m, 2H), 0.89(t, 3H); ESMS Calcd ($C_{28}H_{24}N_4O_3$): 464.18, found: 465.1 $(M+H)^+$.

Compound (42)

$^1$H NMR (DMSO-$d_6$) δ 2.3 (s, 3H), 5.6 (s, 2H), 6.9 (s, 1H), 7.0–7.5 (m, 7H), 8.1 (d, 1H, J=7), 8.65 (s, 1H). ESMS calcd for ($C_{21}H_{17}ClN_4O_2S$): 424.1; found 425.1 $(M+H)^+$.

Compound (43)

$^1$H NMR (DMSO-$d_6$): δ 10.85(s, 1H), 9.09(s, 1H), 8.43(s, 1H), 8.31(d, 1H), 7.97(s, 1H), 7.90(s, 1H), 7.82(d, 2H), 7.63(d, 1H), 7.58(d, 1H), 7.45(d, 2H), 7.42(m, 2H), 7.33(m, 2H), 5.74(s, 2H); ESMS Calcd ($C_{25}H_{18}N_4O_3$): 422.14, found: 423.1 $(M+H)^+$.

Example 3

Compound (1) Demonstrates Anti-Cancer Activity (In Vitro)

The in vitro activity of the compounds was determined in the following seven human cancer cell lines. MDA435 (human breast cancer), HL-60 (human myeloid leukemia), DU-145 (human prostate cancer), MES-SA (human uterine sarcoma), H2 (human leukemia) were obtained from ATCC (American Type of Culture Collection).

The cell lines were maintained in RPMI1640(GIBCO) supplemented with 10% FCS, 100 units/ml penicillin, 100 ug/ml streptomycin, and 2 mM L-glutamine. The cells were split every third day and diluted to a concentration of $2 \times 10^5$ cells/ml one day before experiment. All experiments were performed on exponentially growing cell culture. Cell densities were $2.5 \times 10^4$ cells/ml in all experiment.

A stock solution of Compound (1) was prepared by dissolving the compound at a concentration of 1 mM in 100% DMSO. Final concentrations were obtained by diluting the stock solution directly into the tissue culture medium. Cells were incubated with varying concentrations of compounds for 72 hours and the $IC_{50}$ was determined by MTS (i.e. 3-(4.5.-dimethylthiazol-2-yl)-2.5-diphenyl tetrazolium bromide) assay. $IC_{50}$ stands for the concentration of compound required to inhibit 50% tumor cell growth. The results are shown in Table 1.

TABLE 1

In Vitro Anti-Cancer Activity of Compound (1)

| Cancer Cell Lines | $IC_{50}$ (uM) |
| --- | --- |
| MDA-435 | 0.005 |
| HL-60 | 0.005 |
| DU-145 | 0.005 |
| MES-SA | 0.005 |
| H2 | 0.005 |

As can be seen from the results in Table 1, Compound (1) demonstrated significantly high anti-cancer activity ($IC_{50}$: 0.005 uM) against five cancer cell lines with wide variety of cancer cell types.

Example 4

Compound (1) Demonstrates Anti-Cancer Activity against MDR (Multi Drug Resistant) Cancer Cells (In Vitro)

In vitro activity was determined in two MDR (Multi Drug Resistant) human cancer cell lines. HL-60/TX1000 was isolated in vitro by subculturing HL-60 in progressively higher concentration of Taxol. HL-60/TX1000 cells overexpress mdr-1 mRNA and p-glycoprotein, as determined by western blot and immunofluorescence labeling with antiPGP antibodies. The cell is cross-resistant to Taxol, Vincristine, Adriamycin, Etoposide and Doxorubicin. MES-SA/Dx5 was established in the presence of increasing concentrations of Doxorubicin. The cells express high levels of mdr-1 mRNA and p-glycoprotein and exhibit cross resistance to more than fifteen chemotherapeutic agents including Taxol, Etoposide, Mitomycin C, Colchicine, Vinblastine, Dactinomycin, 5-Fluorouracil and Methotrexate. MES-SA/Dx5 was purchased from ATCC.

The procedure for culturing the cells and assaying cancer cell growth inhibition were as described in Example 3. The results are shown in Table 2.

TABLE 2

In Vitro Anti-Cancer Activity of Compound (1), Taxol (control) and Vincristine (control) Against Multi Drug Resistance Cancer Cell Lines

| Cancer Cell Lines | $IC_{50}$ (uM) | | |
| --- | --- | --- | --- |
| | Compound (1) | Taxol | Vincristine |
| HL-60/TX1000 | 0.01 | 5 | 5 |
| MES-SA/DX-5 | 0.01 | 5 | 1 |

Taxol and Vincristine were not effective ($IC_{50}$: 1–5 uM) against the MDR cell lines (MES-SA/DX5 and HL-60/TX1000). On the other hand, Compound (1) showed high anti-cancer activity against these MDR cancer cell lines.

Example 5
Compound (1) Demonstrates Anti-Cancer Efficacy on Human Breast Tumor (MCF-7) Xenograft Model (In Vivo)

The in vivo anti-cancer efficacy of Compound (1) was assessed in tumor bearing mice using a tumor growth inhibition assay. Human breast tumor (MCF-7) cells were implanted by injection of a tumor cell suspension subcutaneously in the flank of a nude mouse. Treatment of the tumor with an experimental compound began after the tumor had been established (volume was approximately 100 mm$^3$). The animal then began a multiple injection schedule where the compound was administered orally. Tumors were measured two times a week. During the course of this assay, animals were monitored daily for signs of toxicity including body weight loss.

A supplemented media was prepared from 50% DMEM/Dulbecco Modified Eagle Medium (High Glucose), 50% RPMI 1640, 10% FBS/Fetal Bovine Serum (Hybridoma Tested; Sterile Filtered), 1% L-Glutamine, 1% Penicillin-Streptomycin, 1% MEM Sodium Pyruvate, 1% MEM Non-Essential Amino Acids. FBS was obtained from Sigma Chemical Co. and other ingredients were obtained from Invitrogen Life Technologies, USA). The supplemental media was warmed to 37° C. and 50 ml of media was added to a 175 cm$^2$ tissue culture flask.

The cells used in the assay were MCF-7 Human Breast Carcinoma from the American Type Culture Collection. One vial of MCF-7-435 cells from the liquid nitrogen frozen cell stock was removed. The frozen vial of cells was immediately placed into a 37° C. water bath and gently swirled until thawed. The freeze-vial was wiped with 70% ethanol and cells were immediately pipetted into the 175 cm$^2$ tissue culture flask containing supplemented media. The cells were incubated overnight and the media was removed and replaced with fresh supplemented media the next day. The flask was incubated until the flask became about 90% confluent. This typically took about 5–7 days.

The flask was washed with 10 ml of sterile room temperature phosphate buffered saline (PBS). The cells were trypsinized by adding 5 ml of warmed Trypsin-EDTA (Invitrogen) to the flask of cells. The cells were then incubated for 2–3 minutes at 37° C. until cells begun to detach from the surface of the flask. An equal volume of supplemented media (5 ml) was added to the flask. All the cells were collected into 50 ml tube, and centrifuged at 1000 RPM for 5 minutes at 20° C. The supernatant was aspirated and the cell pellet was resuspended in 10 ml of supplemented media and the cells were counted. 1–3 million cells/flask were seeded into 5–7 tissue culture flasks (175 cm$^2$). Each flask contained 50 ml of supplemented media. The flasks were incubated until about 90% confluent. The passaging of the cells was repeated until enough cells have been grown for tumor implantation.

The above procedure for trypsinizing and centrifuging the cells were followed. The supernatant was aspirated and the cell pellet was resuspended in 10 ml of sterile PBS and the cells were counted. The cells were centrifuged and then resuspended with appropriate volume of sterile PBS for injection of correct number of cells needed for tumor implantation. In the case of MCF-7, 100 million cells were suspended with 2.0 ml of sterile PBS to a final concentration of 50 million cells/ml in order to inject 5 million cells in 0.1 ml/mouse.

Mice (CD-1 nu/nu) were obtained from Charles River Laboratories: nomenclature: Crl:CD-1-nuBR, Age: 6–8 weeks. The mice were allowed to acclimate for 1 week prior to their being used in an experimental procedure.

One day before MCF-7 tumor implantation, estradiol pellets were implanted subcutaneously.

Implantation of the MCF-7 tumor cell suspension took place into the corpus adiposum of the female CD-1 nu/nu mouse. This fat body is located in the ventral abdominal viscera of the mouse. Tumor cells were implanted subsutaneously into the fat body located in the right quadrant of the abdomen at the juncture of the os coxae (pelvic bone) and the os femoris (femur). 5 million MCF-7 cells in 0.1 ml of sterile PBS were injected using 27 G (½ inch) needle. MDA-435 tumors developed 2–3 weeks after implantation.

Compound stock solutions were prepared by dissolving the compound in cell-culture grade DMSO (dimethyl sulfoxide) at the desired concentration. This stock solution in DMSO was sonicated in an ultrasonic water bath until all the powder dissolved.

The formulation solvent was prepared as follows: 20% of Cremophor RH40 (Polyoxyl 40 Hydrogenated Castor Oil obtained from BASF corp.) in water was prepared by first heating 100% Cremophor RH40 in a water bath at 50–60° C. until it liquefied and become clear. 10 ml of the 100% Cremophor RH40 aliquoted into a conical centrifuge tube containing 40 ml of sterile water. The 20% Cremophor RH40 solution was reheated until it become clear again.

Preparation of Dosing Solution for Compound Administration: The DMSO compound stock solution was diluted 1:10 with 20% Cremophor RH40. The final formulation for the dosing solution was 10% DMSO, 18% Cremophor RH40 and 72% Water. The dosing solution (Dosing volume: 0.01 ml/gram=10 ml/kg) was injected intravenously into the mice bearing MCF-7 human breast tumor.

Protocol

| Group | Compounds | Dose |
| --- | --- | --- |
| 1 | Vehicle | |
| 2 | Compound (1) | 7.5 mg/kg |
| 3 | Compound (1) | 10 mg/kg |

Dosing schedule: 3 times a week (Monday, Wednesday, Friday) for 3 weeks mice were used for each group.

Figure 1:
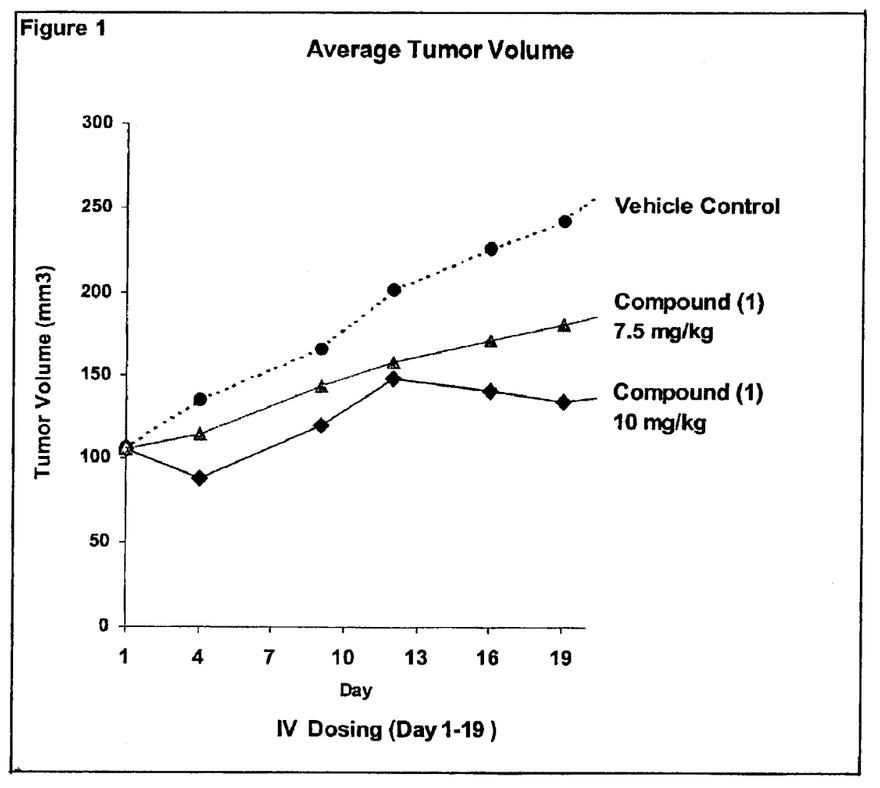
FIG. 1 is a graph depicting the anti-tumor effects of Compound (1) administered intravenously to nude mice with human breast MCF-7 tumors. The graph shows the volume of the tumors in mm³ over time in days after the beginning of dosing with vehicle, 7.5 mg/kg per every second day of Compound (1) and 10 mg/kg every second day of Compound (1).

FIG. 1 shows the anti-tumor efficacy of Compound (1). As can be seen from FIG. 1, Compound (1) significantly inhibits tumor growth of MCF-7 in nude mice at 7.5 and 10 mg/kg in a dose-dependent manner with acceptable toxicity.

Example 6
Compounds (2)–(10) Demonstrates High Anti-Cancer Activity against MES-SA/DX5 and HL60/TX1000 (In Vitro)

The protocol described in Example 3 was used to assay inhibition by Compounds (2)–(10) on the growth of the multi-drug resistant cell lines MES-SA/DX5 and HL60/TX1000. The results are shown in Table 3.

TABLE 3

In Vitro Anti-Cancer Activity of Compound (2)–(10) against Multi-Drug Resistance Human Cell Lines, MES-SA/DX5 and HL60/TX1000

| Compound | $IC_{50}$ (uM) MES-SA/DX5 | $IC_{50}$ (uM) HL-60/TX1000 |
|---|---|---|
| (2) | 0.005 | 0.005 |
| (3) | 0.05 | 0.05 |
| (4) | 0.05 | 0.05 |
| (5) | 0.05 | 0.05 |
| (6) | 0.05 | 0.05 |
| (7) | 0.08 | 0.05 |
| (8) | 0.1 | 0.1 |
| (9) | 0.05 | 0.05 |
| (10) | 0.05 | 0.05 |

Compounds (2)–(10) demonstrated significant anti-cancer activity ($IC_{50}$: 0.005–0.1 uM) against MES-SA/DX5 and HL60/TX1000, while Taxol showed very weak anti-cancer activity (IC50: 5 uM) against the MDR cell lines.

Example 7

Compounds (3) and (5) Demonstrates Anti-Cancer Efficacy on Human Breast Tumor (MDA435) Xenograft Model with Oral Treatment (in vivo)

The in vivo anti-cancer efficacy of Compounds (3) and (5) was assessed in tumor bearing mice using the tumor growth inhibition assay described in Example 5, except that the compounds were administered orally by gavage.

Protocol

| Group | Compounds | Dose |
|---|---|---|
| 4 | Vehicle | |
| 5 | Compound (5) | 25 mg/kg |
| 6 | Compound (3) | 50 mg/kg |

Dosing schedule: 3 times a week (Monday, Wednesday, Friday) for 3 weeks 5 mice were used for each group.

Figure 2:
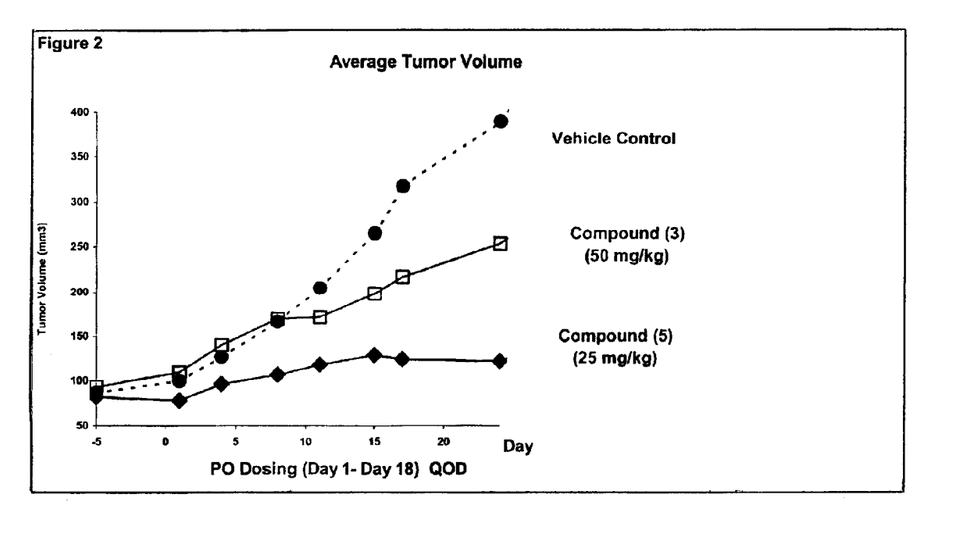
FIG. 2 is a graph depicting the anti-tumor effects of Compounds (3) and (5) administered orally to nude mice with human breast MDA435 tumors. The graph shows the volume of the tumors in mm$^3$ over time in days after the beginning of dosing with vehicle, 50 mg/kg per every second day of Compound (3) and 25 mg/kg every second day of Compound (5).

FIG. 2 shows the anti-tumor efficacy of Compounds (3) and (5). As can be seen from FIG. 2, Compounds (5) and (3) significantly inhibit tumor growth of MDA435 in nude mice at 25 mg/kg and 50 mg/kg respectively without showing significant body weight loss of mice.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by the following structural formula:

or a pharmaceutically acceptable salt thereof, wherein:

Ring A is substituted or unsubstituted and is optionally fused to an aryl group;

$Z_1$ and $Z_2$ are independently =O, =S, =N—$OR_9$ or =$NR_9$;

$R_4$ is —H, a substituted alkyl group or an unsubstituted alkyl group;

$R^9$ is —H or a substituted or unsubstituted alkyl group;

each $R_{15}$ is independently —Br, —Cl, —F, —$R_{18}$, —$OR_{18}$, —CN, —$COOR_{18}$, —$N(R_{18})_2$, —$CON(R_{18})_2$, —$NR_{18}COR_{19}$, —$NHCONH_2$ or —$SO_2$ $N(R_{18})_2$;

n is an integer from 1–4;

$R_{16}$ and $R_{17}$ are independently —H, an aliphatic group, a substituted aliphatic group, an unsubstituted non-aromatic heterocyclic group, a substituted non-aromatic heterocyclic group, an unsubstituted carbocyclic aryl group, a substituted carbocyclic aryl group; a substituted or unsubstituted imidazolyl, a substituted or unsubstituted isoimidazolyl, a substituted or unsubstituted thienyl, a substituted or unsubstituted furanyl, a substituted or unsubstituted pyridyl, a substituted or unsubstituted pyranyl, a substituted or unsubstituted pyrrolyl, a substituted or unsubstituted pyrazinyl, a substituted or unsubstituted isothiazolyl, a substituted or unsubstituted oxazolyl, a substituted or unsubstituted isoxazolyl, a substituted or unsubstituted 1,2,3-triazolyl, a substituted or unsubstituted 1,2,4-triazolyl, a substituted or unsubstituted tetrazolyl, a substituted or unsubstituted benzothienyl, a substituted or unsubstituted benzofuranyl, a substituted or unsubstituted indolyl, a substituted or unsubstituted quinolinyl, a substituted or unsubstituted benzothiazolyl, a substituted or unsubstituted benzoisothiazolyl, a substituted or unsubstituted benzoxazolyl, a substituted or unsubstituted benzoisoxazolyl, a substituted or unsubstituted benzoimidazolyl, a substituted or unsubstituted quinolinyl, a substituted or unsubstituted isoquinolinyl or a substituted or unsubstituted isoindolyl; or —$NR_{16}R_{17}$, taken together, is a substituted or unsubstituted non-aromatic nitrogen-containing heterocyclic group or a substituted or unsubstituted nitrogen-containing heteroaryl group; and $R_{18}$ and $R_{19}$ are independently —H, alkyl or substituted alkyl.

2. The compound of claim 1 wherein:
Ring A is substituted or unsubstituted;
$Z_1$ and $Z_2$ are =O;
$R_4$ is —H;
each $R_{15}$ is independently —Cl, —F, —$R_{18}$, —$OR_{18}$, —CN, —$NH_2$, —$CONH_2$ or —$NHCOR_{18}$;
n is 0 or 1;
$R_{16}$ is —H;
$R_{17}$ is a substituted or unsubstituted aryl group; and
$R_{18}$ is a C1–C4 alkyl group.

3. The compound of claim 2 wherein:
Ring A is substituted with zero, one or more groups selected from —F, —Cl, —Br, —C1–C4 alkyl, C1–C4 alkoxy, —C1–C4 haloalkyl, C1–C4 haloalkoxy, —CN and —$NH_2$; and
$R_{17}$ is a substituted or unsubstituted phenyl, quinolinyl, or pyridyl group.

4. The compound of claim 3 wherein n is 0; and $R_{17}$ is pyridyl.

5. The compound of claim 4 wherein $R_{17}$ is 4-pyridyl.

6. A method of treating a subject with cancer, said method comprising administering to the subject an effective amount of a compound represented by the following structural formula:

or a pharmaceutically acceptable salt thereof, wherein:
Ring A is substituted or unsubstituted and is optionally fused to an aryl group;
$Z_1$ and $Z_2$ are independently =O, =S, =N—$OR_9$ or =$NR_9$;
$R_4$ is —H, a substituted alkyl group or an unsubstituted alkyl group;
$R_9$ is —H or a substituted or unsubstituted alkyl group;
each $R_{15}$ is independently —Br, —Cl, —F, —$R_{18}$, —$OR_{18}$, —CN, —$COOR_{18}$, —$N(R_{18})_2$, —$CON(R_{18})_2$, —$NR_{18}COR_{19}$, —$NHCONH_2$ and —$SO_2N(R_{18})_2$;
n is an integer from 1–4;
$R_{16}$ and $R_{17}$ are independently —H, an aliphatic group, a substituted aliphatic group, an unsubstituted non-aromatic heterocyclic group, a substituted non-aromatic heterocyclic group, an unsubstituted carbocyclic aryl group, a substituted carbocyclic aryl group; a substituted or unsubstituted imidazolyl, a substituted or unsubstituted isoimidazolyl, a substituted or unsubstituted thienyl, a substituted or unsubstituted furanyl, a substituted or unsubstituted pyridyl, a substituted or unsubstituted pyranyl, a substituted or unsubstituted pyrrolyl, a substituted or unsubstituted pyrazinyl, a substituted or unsubstituted isothiazolyl, a substituted or unsubstituted oxazolyl, a substituted or unsubstituted isoxazolyl, a substituted or unsubstituted 1,2,3-triazolyl, a substituted or unsubstituted 1,2,4-triazolyl, a substituted or unsubstituted tetrazolyl, a substituted or unsubstituted benzothienyl, a substituted or unsubstituted benzofuranyl, a substituted or unsubstituted indolyl, a substituted or unsubstituted quinolinyl, a substituted or unsubstituted benzothiazolyl, a substituted or unsubstituted benzoisothiazolyl, a substituted or unsubstituted benzoxazolyl, a substituted or unsubstituted benzoisoxazolyl, a substituted or unsubstituted benzoimidazolyl, a substituted or unsubstituted quinolinyl, a substituted or unsubstituted isoquinolinyl or a substituted or unsubstituted isoindolyl; or —$NR_{16}R_{17}$, taken together, is a substituted or unsubstituted non-aromatic nitrogen-containing heterocyclic group or a substituted or unsubstituted nitrogen-containing heteroaryl group; and
$R_{18}$ and $R_{19}$ are independently —H, alkyl or substituted alkyl, wherein the cancer is human breast cancer, human myeloid leukemia, human uterine sarcoma, human prostate cancer, human leukemia, or a multidrug resistant strain thereof.

7. The method of claim 6 wherein:
Ring A is substituted or unsubstituted;
$Z_1$ and $Z_2$ are =O;
$R_4$ is —H;
each $R_{15}$ is independently —Cl, —F, —$R_{18}$, —$OR_{18}$, —CN, —$NH_2$, —$CONH_2$ or —$NHCOR_{18}$;
n is 0 or 1;
$R_{16}$ is —H;
$R_{17}$ is a substituted or unsubstituted aryl group; and
$R_{18}$ is a C1–C4 alkyl group.

8. The method of claim 7 wherein:
Ring A is substituted with zero, one or more groups selected from —F, —Cl, —Br, —C1–C4 alkyl, C1–C4 alkoxy, —C1–C4 haloalkyl, C1–C4 haloalkoxy, —CN and —$NH_2$; and
$R_{17}$ is a substituted or unsubstituted phenyl, quinolinyl, or pyridyl group.

9. The method of claim 8 wherein n is 0; and $R_{17}$ is pyridyl.

10. The method of claim 9 wherein $R_{17}$ is 4-pyridyl.

11. The method of claim 6 wherein the cancer is multidrug resistant.

12. A pharmaceutical composition, comprising a pharmaceutically acceptable carrier or diluent and a compound represented by the following structural formula:

Ring A is substituted or unsubstituted and is optionally fused to an aryl group;

$Z_1$ and $Z_2$ are independently =O, =S, =N—$OR_9$ or =$NR_9$;

$R_4$ is —H, a substituted alkyl group or an unsubstituted alkyl group;

$R_9$ is —H or a substituted or unsubstituted alkyl group;

each $R_{15}$ is independently —Br, —Cl, —F, —$R_{18}$, —$OR_{18}$, —CN, —$COOR_{18}$, —$N(R_{18})_2$, —$CON(R_{18})_2$, —$NR_{18}COR_{19}$, —$NHCONH_2$ or —$SO_2 N(R_{18})_2$;

n is an integer from 1–4;

$R_{16}$ and $R_{17}$ are independently —H, an aliphatic group, a substituted aliphatic group, an unsubstituted non-aromatic heterocyclic group, a substituted non-aromatic heterocyclic group, an unsubstituted carbocyclic aryl group, a substituted carbocyclic aryl group; a substituted or unsubstituted imidazolyl, a substituted or unsubstituted isoimidazolyl, a substituted or unsubstituted thienyl, a substituted or unsubstituted furanyl, a substituted or unsubstituted pyridyl, a substituted or unsubstituted pyranyl, a substituted or unsubstituted pyrrolyl, a substituted or unsubstituted pyrazinyl, a substituted or unsubstituted isothiazolyl, a substituted or unsubstituted oxazolyl, a substituted or unsubstituted isoxazolyl, a substituted or unsubstituted 1,2,3-triazolyl, a substituted or unsubstituted 1,2,4-triazolyl, a substituted or unsubstituted tetrazolyl, a substituted or unsubstituted benzothienyl, a substituted or unsubstituted benzofuranyl, a substituted or unsubstituted indolyl, a substituted or unsubstituted quinolinyl, a substituted or unsubstituted benzothiazolyl, a substituted or unsubstituted benzoisothiazolyl, a substituted or unsubstituted benzoxazolyl, a substituted or unsubstituted benzoisoxazolyl, a substituted or unsubstituted benzoimidazolyl, a substituted or unsubstituted quinolinyl, a substituted or unsubstituted isoquinolinyl or a substituted or unsubstituted isoindolyl; or —$NR_{16}R_{17}$, taken together, is a substituted or unsubstituted non-aromatic nitrogen-containing heterocyclic group or a substituted or unsubstituted nitrogen-containing heteroaryl group; and $R_{18}$ and $R_{19}$ are independently —H, alkyl or substituted alkyl.

13. The composition of claim 12 wherein:

Ring A is substituted or unsubstituted;

$Z_1$ and $Z_2$ are =O;

$R_4$ is —H;

each $R_{15}$ is independently —Cl, —F, —$R_{18}$, —$OR_{18}$, —CN, —$NH_2$, —$CONH_2$ or —$NHCOR_{18}$;

n is 0 or 1;

$R_{16}$ is —H;

$R_{17}$ is a substituted or unsubstituted aryl group; and $R_{18}$ is a C1–C4 alkyl group.

14. The composition of claim 13 wherein:

Ring A is substituted with zero, one or more groups selected from —F, —Cl, —Br, —C1–C4 alkyl, C1–C4 alkoxy, —C1–C4 haloalkyl, C1–C4 haloalkoxy, —CN and —$NH_2$; and $R_{17}$ is a substituted or unsubstituted phenyl, quinolinyl, or pyridyl group.

15. The composition of claim 14 wherein n is 0; and $R_{17}$ is pyridyl.

16. The composition of claim 15 wherein $R_{17}$ is 4-pyridyl.

* * * * *